(12) United States Patent
Adamczyk et al.

(10) Patent No.: US 9,889,271 B2
(45) Date of Patent: Feb. 13, 2018

(54) SYSTEM, APPARATUS AND METHOD FOR TREATING SLEEP DISORDER SYMPTOMS

(71) Applicant: Intelclinic LLC, San Francisco, CA (US)

(72) Inventors: Kamil Adamczyk, Warsaw (PL); Janusz Fraczek, Warsaw (PL)

(73) Assignee: Inteliclinic Inc., San Francisco, CA (US)

( * ) Notice: Subject to any disclaimer, the term of this patent is extended or adjusted under 35 U.S.C. 154(b) by 616 days.

(21) Appl. No.: 14/589,922

(22) Filed: Jan. 5, 2015

(65) Prior Publication Data

US 2016/0193442 A1   Jul. 7, 2016

(51) Int. Cl.
*A61M 21/00* (2006.01)
*A61M 21/02* (2006.01)
*A61N 5/06* (2006.01)

(52) U.S. Cl.
CPC .......... *A61M 21/02* (2013.01); *A61N 5/0618* (2013.01); *A61M 2021/0044* (2013.01); *A61M 2205/332* (2013.01); *A61M 2205/3303* (2013.01); *A61M 2205/3306* (2013.01); *A61M 2205/3584* (2013.01); *A61M 2205/50* (2013.01); *A61M 2210/0612* (2013.01); *A61M 2230/06* (2013.01); *A61M 2230/10* (2013.01); *A61M 2230/14* (2013.01); *A61M 2230/205* (2013.01); *A61M 2230/50* (2013.01); *A61M 2230/60* (2013.01); *A61M 2230/63* (2013.01); *A61N 2005/0626* (2013.01); *A61N 2005/0651* (2013.01)

(58) Field of Classification Search
CPC ............................. A61M 21/02; A61N 5/0618

USPC ...................................................... 600/26–28
See application file for complete search history.

(56) References Cited

U.S. PATENT DOCUMENTS

| | | | |
|---|---|---|---|
| 4,858,609 A | 8/1989 | Cole | |
| 5,006,985 A | 4/1991 | Ehret et al. | |
| 5,163,426 A | 11/1992 | Czeisler et al. | |
| 5,259,830 A | 11/1993 | Masuda | |
| 5,304,212 A | 4/1994 | Czeisler et al. | |
| 5,507,716 A | 4/1996 | Laberge et al. | |
| 7,179,218 B2 | 2/2007 | Raniere | |
| 7,956,756 B2 | 6/2011 | Kubey et al. | |
| 8,303,635 B2 | 11/2012 | Hurst | |
| 8,556,951 B2 | 10/2013 | Witt et al. | |

(Continued)

OTHER PUBLICATIONS

International Search Report, dated Feb. 26, 2016, for corresponding International Application No. PCT/US2016/012090.

(Continued)

*Primary Examiner* — John Lacyk
(74) *Attorney, Agent, or Firm* — Intellectual Property Law Group LLP

(57) ABSTRACT

A system, apparatus and method for treating or lessening sleep disorder symptoms. The system comprising a mask configured to establish a snug fit against a user's eyes and a device including a data management system and a user interface, wherein the device is coupled to the mask. The mask includes a printed circuit board, an accelerometer, one or more therapy lights, one or more electrodes, a pulse oximeter, and a thermometer, wherein the pulse oximeter, thermometer, accelerometer, and electrodes are connected to the printed circuit board, collect data, and send data to the printed circuit board. The device generates a light therapy schedule based on data received from the user through the user interface and data from the mask.

18 Claims, 9 Drawing Sheets

(56) References Cited

U.S. PATENT DOCUMENTS

| | | |
|---|---|---|
| 8,639,313 B2 | 1/2014 | Westbrook et al. |
| 8,784,293 B2 | 7/2014 | Berka et al. |
| 2007/0002692 A1 | 1/2007 | Brunt |
| 2011/0257467 A1 | 10/2011 | Clegg et al. |
| 2012/0083673 A1 | 4/2012 | Al-Ali et al. |
| 2012/0137406 A1 | 6/2012 | Hide |
| 2012/0209355 A1 | 8/2012 | Witt et al. |
| 2013/0060306 A1 | 3/2013 | Colbauch |
| 2013/0178920 A1 | 7/2013 | Holley et al. |
| 2013/0324788 A1 | 12/2013 | Givertz et al. |
| 2014/0221779 A1 | 8/2014 | Schoonover et al. |

OTHER PUBLICATIONS

Written Opinion of the International Searching Authority, dated Feb. 26, 2016, for corresponding International Application No. PCT/US2016/012090.

SYSTEM, APPARATUS AND METHOD FOR TREATING SLEEP DISORDER SYMPTOMS

BACKGROUND OF THE INVENTION

1. Field of the Invention

Aspects of the present invention relate to a system, apparatus and method for treating or lessening sleep disorder symptoms. In particular, there is a light therapy mask coupled to a device having a data management system.

2. Background

Without limiting the scope of the invention, the present background is described in connection of treating or lessening sleep disorder symptoms. A circadian rhythm is any biological process that displays an endogenous, entrainable oscillation of about 24 hours. These rhythms are driven by a circadian clock, and rhythms have been widely observed in plants, animals, fungi, and cyanobacteria. Although circadian rhythms are endogenous ("built-in", self-sustained), they are adjusted (entrained) to the local environment by external cues called zeitgebers, commonly the most important of which is daylight.

The master network coordinating our circadian clock is based in the suprachiasmatic nucleus (SCN) of the hypothalamus, where neurons exhibit circadian rhythms in their electrical activity and are driven by cell-autonomous molecular feedback loops. These neural activity rhythms are critical for circadian output and are reciprocally required for the sustained generation of their own internal molecular oscillations. Output from this SCN clock regulates oscillatory sleep and arousal control centers, leading downstream to the organization of our daily sleep-wake behavior.

Retinal light exposure is the preeminent synchronizer of circadian rhythms in mammals, including humans.

Human alertness demonstrates a circadian rhythmicity with a seemingly paradoxical nadir of sleepiness at the end of the day (the "Maintenance of Wakefulness Zone"), followed by a peak in difficulty sustaining wakefulness in the second third of the sleep period (approximately 3-5 A.M.) and then a gradual in-crease in alertness until the next evening. Pineal release of melatonin is stimulated by the suprachiasmatic nucleus of the hypothalamus (SCN) starting about 1-2 h before habitual sleep onset time and continuing through the night, unless such stimulation is masked by light of more than 50-100 lx intensity.

The International Classification of Sleep Disorders lists approximately 60 disorders of human sleep including circadian rhythm sleep disorders (CRSD). CRSD usually present as a social problem in a person's sleep/wake timing. The most common complaints for CRSD are difficulty initiating or ending sleep at appropriate social times.

Circadian rhythm sleep disorders are classified into the following types according to the American Academy of Sleep Medicine: advanced sleep phase disorder (ASPD), delayed sleep phase disorder (DSPD), free-running sleep disorder (FRSD), irregular sleep-wake disorder (ISWD), jet lag disorder, and shift work disorder.

There is no fully automated, non-invasive method, currently available on the market, for treating circadian rhythms disorders. Commercially available solutions are ineffective, impractical or unwieldy.

There is accordingly a need for a solution to be fully automated, non-invasive to the user and handy such that the system could be used in all conditions, especially at work or while traveling.

There is a need to obtain benefits of using a system that will completely cure or minimize the disturbance caused by abnormal circadian rhythms (e.g. jet lag), such as: poor sleep during new night-times, including delayed sleep onset (after eastward flights), early awakening (after westward flights), and fractionated sleep (after flights in either direction); poor performance during the new daytimes at both physical and mental tasks; negative subjective changes (these include increased fatigue, higher frequency of headaches and irritability, and a decreased ability to concentrate); and gastrointestinal disturbances (indigestion, the frequency of defecation, and the consistency of the stools) and decreased interest in, and enjoyment of, meals.

Another problem to be addressed is to solve the automatic detection of sleep apnea, particularly in the patient's home.

Sleep apnea (SA) is a common sleep disorder characterized by multiple cessations of breathing during sleep that lead to intermit-tent hypoxia and sleep fragmentation. Each apnea, the period of the cessation of breathing, can last from 10 s to several minutes. The severity of SA is categorized as mild, moderate, or severe, based on the number of apneas per hour, and it is the most frequent medical cause of daytime sleepiness. Untreated SA has been shown to increase the risk of motor vehicle accidents, and evidence indicates that SA is a risk factor for diabetes and cardiovascular disease-related mortality and morbidity.

There are many devices on the market that examine sleep apnea in the patient's home. They measure biological parameters such as finger pulse oximetry, movements of the chest, airflow in the mouth/nose. However, in order to determine sleep apnea, a sleep study is required to conclude that when the breathing has stopped the patient was asleep.

Accordingly, there is a further need for a system, apparatus and method that will automatically stage the patient's sleep, so one will be sure that the sleep apnea occurred during sleep or when the patient was awake.

SUMMARY OF THE INVENTION

Embodiments of the present invention provide a system for lessening sleep disorder symptoms, comprising a mask and a device equipped with a data management system and a data management system user interface. The data management system is configured to generate a light therapy schedule based on personalized information from the user.

According to an embodiment of the present invention, there is a system for treating sleep disorder symptoms, the system comprising: a mask including a printed circuit board, a case, one or more electrodes, a thermometer, a pulse oximeter, and a plurality of light apertures; and a device including a user interface and a data management system. The mask is configured to establish a snug fit against a user's eyes. The printed circuit board includes an accelerometer and one or more therapy lights. The case is configured to house the printed circuit board, and the case includes a power button, a power input port, one or more electrodes, a pulse oximeter, a thermometer, and a plurality of light apertures. The power input port is configured to supply power to the printed circuit board from an external power source. The plurality of light apertures are positioned substantially opposite the user's eyes, such that when the mask is worn, light from the one or more therapy lights passes through the plurality of light apertures to reach the user's eyes. The one or more electrodes, the pulse oximeter, and the thermometer are configured to be positioned on the user's forehead when the mask is worn. The pulse oximeter, the thermometer, and the one or more electrodes are connected to the printed circuit board, configured to measure data including a body temperature of a user, and transmit data to the printed circuit board. The mask is made of an opaque light-blocking material. The device is coupled to the mask. The data management system that is configured to generate a schedule based on a current user sleep schedule and a target user sleep schedule and adjust the schedule based on data received from the mask. The schedule controls operation and light intensity of the one or more therapy lights.

In another embodiment of the present invention, there is a system for treating sleep disorder symptoms, the system comprising: a mask including a printed circuit board, a case, one or more electrodes, a pulse oximeter, a thermometer, and a plurality of light apertures; and a data management system. The mask is configured to establish a snug fit against a user's eyes. The printed circuit board includes an accelerometer and one or more therapy lights. The case is configured to house the printed circuit board. The one or more electrodes, the pulse oximeter, and the thermometer are configured to be positioned on the user's forehead when the mask is worn. The pulse oximeter, the thermometer, and the one or more electrodes are connected to the printed circuit board, configured to measure data including a body temperature of a user, and transmit data to the printed circuit board. The mask is made of an opaque light-blocking material. The data management system is configured to generate a schedule based on a current user sleep schedule and a target user sleep schedule and adjust the schedule based on data received from the mask. The schedule controls operation and light intensity of the one or more therapy lights.

According to an embodiment, there is a sleep mask apparatus for use in a system for treating sleep disorder symptoms. The sleep mask apparatus comprises: a body including a front body side, a back body side, a cavity at the center of the body, a mask strap, a case for housing a printed circuit board, and a power input port operatively connected to the printed circuit board and configured to supply power to the printed circuit board from an external power source. The printed circuit board includes an accelerometer and one or more lights. The case is removably inserted into the cavity, the cavity includes one or more cavity magnets attached to an inside surface of the cavity. The case further comprises a sensor strap wherein one or more dry electrodes, a pulse oximeter and a thermometer are located on the sensor strap. The dry electrodes, pulse oximeter and thermometer sit on movable tabs by way of a spring inside each tab, adjusting for the pressure of the mask against the user's forehead. The pulse oximeter, the thermometer, and the one or more dry electrodes are connected to the printed circuit board and configured to transmit collected data to the printed circuit board. The case further comprising a plurality of light apertures on the case. Two eye apertures are on the back body side, positioned substantially opposite the user's eyes and are substantially aligned with the plurality of light apertures when the mask is worn. The mask is configured to communicate with an external computing device having a data management system.

In another embodiment, there is a method for treating sleep disorder systems using a sleep mask on a user, the method comprising: receiving data from an accelerometer on the sleep mask, receiving data from a thermometer on the sleep mask and, receiving signals from one or more electrodes on the sleep mask; calculating an average time when the user reaches a lowest body temperature; generating a light therapy schedule and adjusting the schedule based on periodically received data including temperature data of the user; controlling and operating a light intensity of one or more lights on the sleep mask. The method further comprises adjusting the schedule by the periodically received data which further includes current sleep stage data as receiving through the signals of the electrodes on the sleep mask. The method further comprises: receiving through a pulse oximeter on the sleep mask, data on pulse and oxygen saturation in the blood; filtering the data and calculating pulse; and calculating oxygen saturation in the blood.

These and other embodiments of the present invention are further made apparent, in the remainder of the present document, to those of ordinary skill in the art.

BRIEF DESCRIPTION OF THE DRAWINGS

In order to more fully describe embodiments of the present invention, reference is made to the accompanying drawings. These drawings are not to be considered limitations in the scope of the invention, but are merely illustrative.

DETAILED DESCRIPTION OF SPECIFIC EMBODIMENTS

The description above and below and the drawings of the present document focus on one or more currently preferred embodiments of the present invention and also describe some exemplary optional features and/or alternative embodiments. The description and drawings are for the purpose of illustration and not limitation. Those of ordinary skill in the art would recognize variations, modifications, and alternatives. Such variations, modifications, and alternatives are also within the scope of the present invention. Section titles are terse and are for convenience only.

Figure 1:
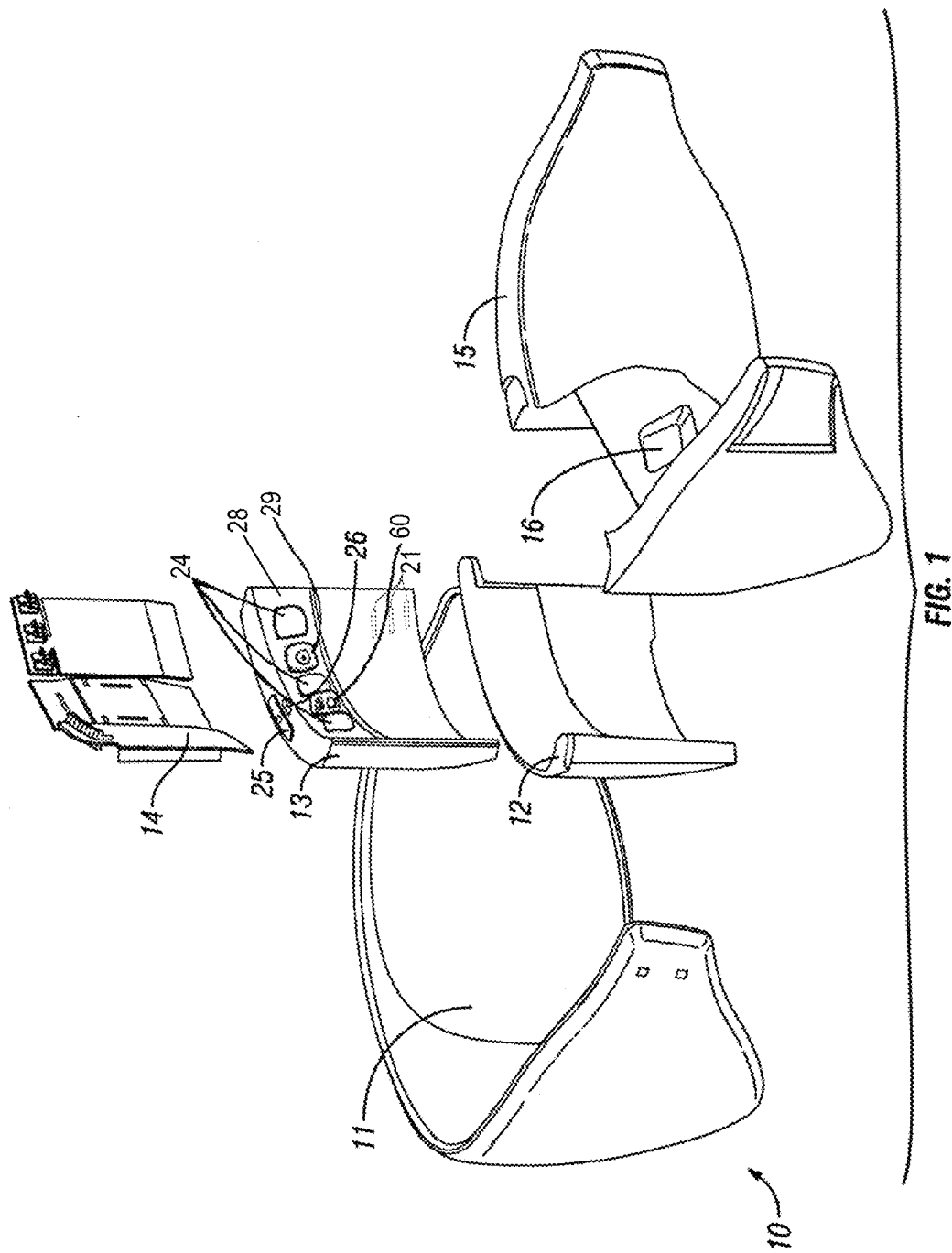
FIG. 1 illustrates an exploded view of the mask, according to an embodiment of the present invention.

FIG. 1 illustrates one embodiment of a mask 10 in exploded view for use in a system in treating sleep disorders. The mask is coupled to a data management system. In a preferred embodiment, the data management system is in a device (not shown). The device is a portable computing device, such as a mobile phone/smartphone, tablet, computer, etc.; and the data management system comprises a computer program/software application, designed to run on a mobile device, tablet computer, smartphone, etc. The mask 10 comprises a body including a front body side 11, a back body side 15, a cavity 12 at the center of the body, a mask strap 41 (not shown), and a case 13 housing a printed circuit board 14. The case is introduced into the cavity 12 from the top. The cavity 12 includes one or more cavity magnets (not shown) attached to the bottom of the cavity 12. Two eye apertures 16 are on the back body side 15. The front body side 11, the back body side 15, and the cavity are permanently connected. The case 13 housing the printed circuit board 14 may be detached from the mask 10. The front body side 11, the back body side 15, the cavity 12, and the mask strap 41 may be washed or sterilized.

According to one or more embodiments, the front body side 11 and the back body side 15 are made of an opaque, light-blocking material. In a preferred embodiment, the front body side 11 is made of soft plastic and the back body side 15 is made of pliable material to establish a snug fit of the body against the user's eyes, thus preventing light in the surroundings from reaching the user. In one or more embodiments, the back body side 15 is made of fabric and viscoelastic foam or thermoformed foam. In a further embodiment, the cavity 12 is made of rigid material. In a preferred embodiment, the cavity 12 is made of hard plastic.

Figure 2A:
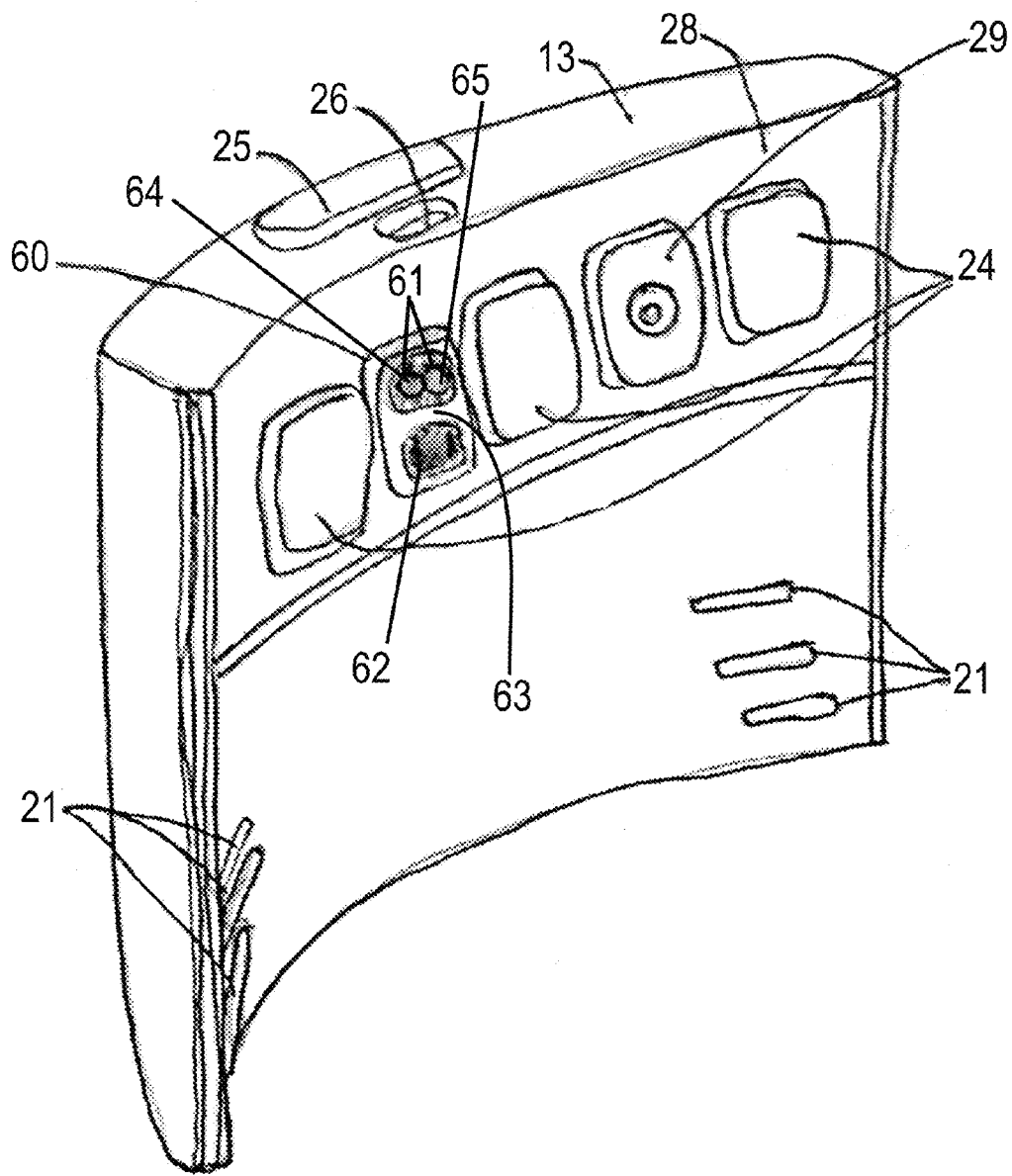
FIG. 2A illustrates a back, top perspective view of the case, according to an embodiment of the present invention.
Figure 3:
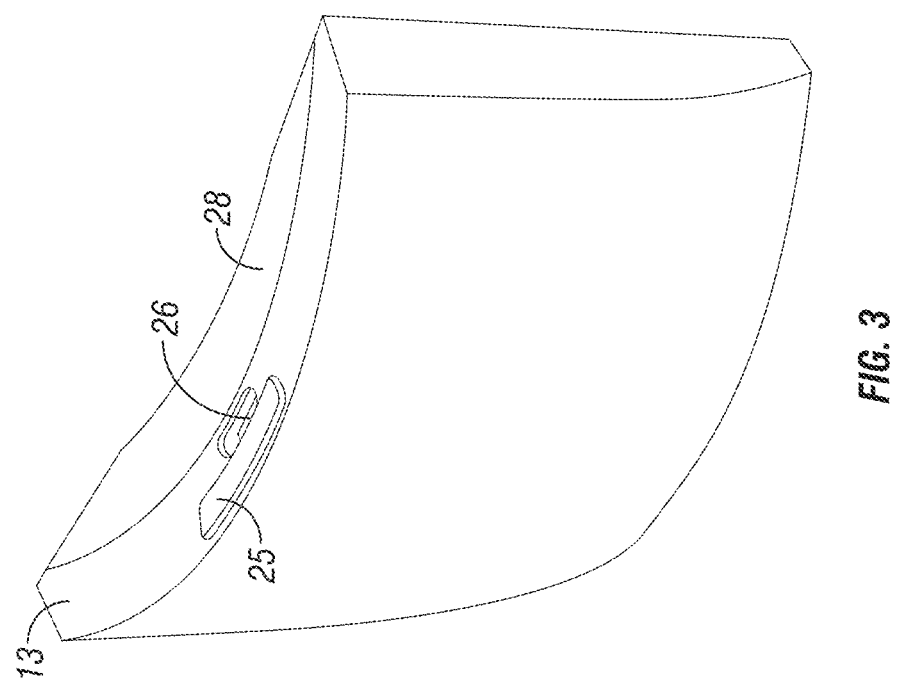
FIG. 3 illustrates a front, top perspective view of the case, according to an embodiment of the present invention.

FIGS. 2A and 3 illustrate one embodiment of the case 13, in a back and front perspective view respectively. The case 13 comprises a power button 25 and a power input port 26 on the top side of the case 13, a sensor strap 28 and a plurality of light apertures 21 on the concave side of the case 13, and one or more case magnets (not shown) attached at the bottom of the case 13. The one or more case magnets (not shown) are aligned with and attracted to the one or more case magnets (not shown), thereby releasably securing the case 13 inside the cavity 12. In a preferred embodiment, a first case magnet (not shown) is attached at the right side of the bottom of the case 13 and a second case magnet (not shown) is attached at the left side of the bottom of the case 13. In one or more embodiments, the sensor strap 28 is made of soft rubber, plastic, or foam.

According to one or more embodiments, the case 13 houses a status indication apparatus (not shown) for the mask 10. The status indication apparatus includes an illumination device for illuminating the power button 25. The power button 25 indicates whether the battery status is charged and whether the mask 10 is connected to the device (not shown). The power button 25 is connected to the printed circuit board 14.

In one or more embodiments, the power input port 26 is configured to supply power to the printed circuit board 14 from an external power source. The power input port 26 is operatively connected to the printed circuit board 14. In a preferred embodiment, the power input port 26 includes a micro-USB (universal serial bus) port (not shown), where the micro-USB port (not shown) is configured to receive a micro-USB connector.

According to one or more embodiments, the sensor strap 28 includes one or more electrodes 24, a pulse oximeter 60, and a thermometer 29. The sensor strap 28 may be permanently attached to the case 13 or may be detachable. The thermometer 29 collects data for body temperature and the pulse oximeter 60 collects data for pulse and oxygen saturation in the blood. In one or more embodiments, the pulse oximeter 60 and the thermometer 29 may collect data with a maximum distance of two centimeters between the user's forehead and the pulse oximeter 60 and the thermometer 29, respectively. In a further embodiment, the pulse oximeter 60 includes two or more photoemitters 61, a photodetector 62, and a partition 63, where one of the two photoemitters is configured to emit red light 64 and one of the two photoemitters is configured to emit infrared light 65. In a preferred embodiment, the sensor strap includes three electrodes 24 and the electrodes 24 are dry electrodes. The thermometer 29 is configured to be positioned between two of the electrodes 24 and the pulse oximeter 60 is configured to be positioned between two of the electrodes 24. In a further embodiment, the electrodes 24 are made of acid resistant steel, conductive polymer, conductive foam, conductive plastic, or conductive fabric. The one or more electrodes 24, the pulse oximeter 60, and the thermometer 29 are connected to the printed circuit board 14.

Figure 2B:
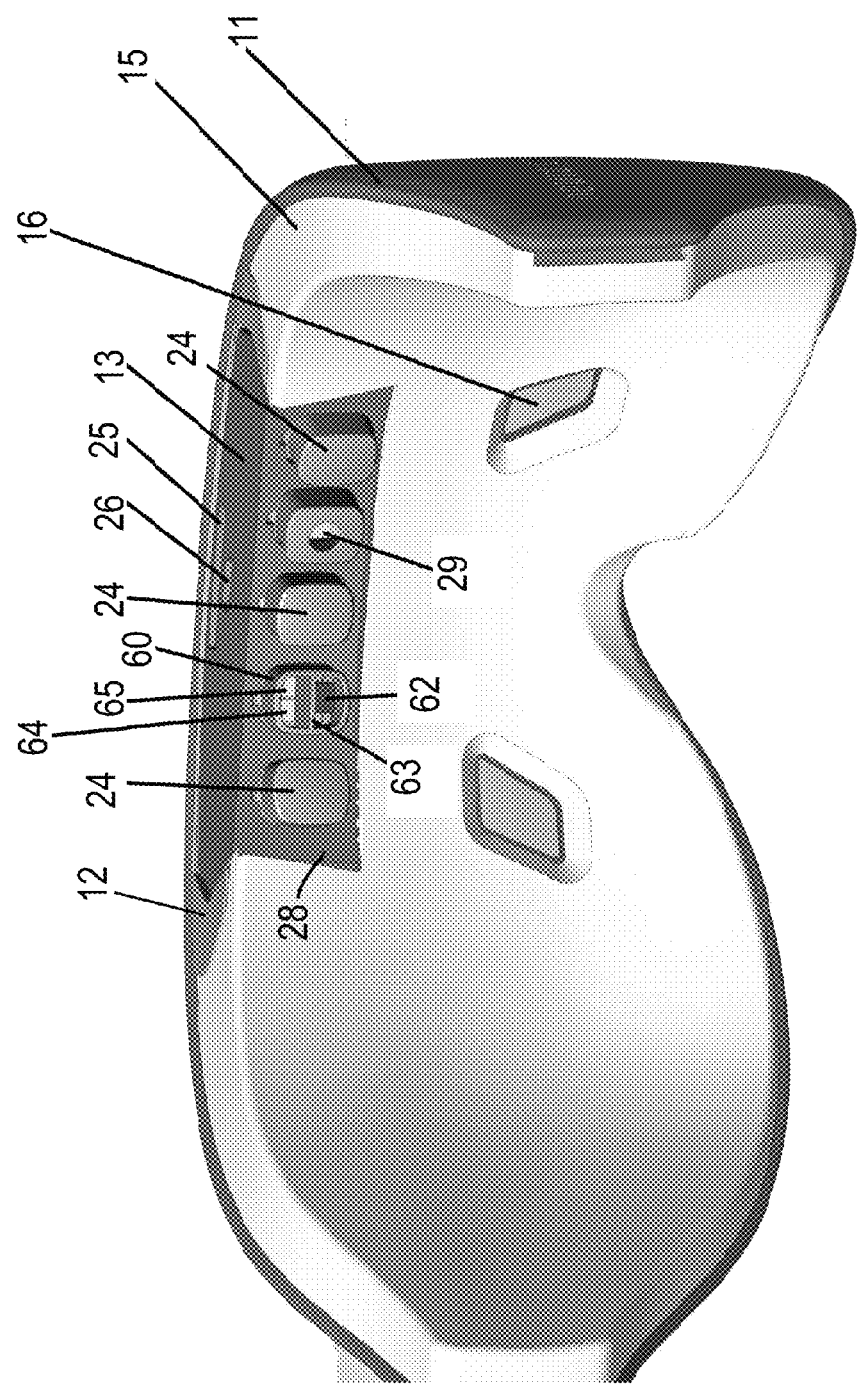
FIG. 2B illustrates a back, top assembled view of the mask, according to an embodiment of the present invention.

FIG. 2B illustrates a back, top assembled view of the mask with the case releasably secured inside the cavity, according to an embodiment of the present invention.

Figure 2C:
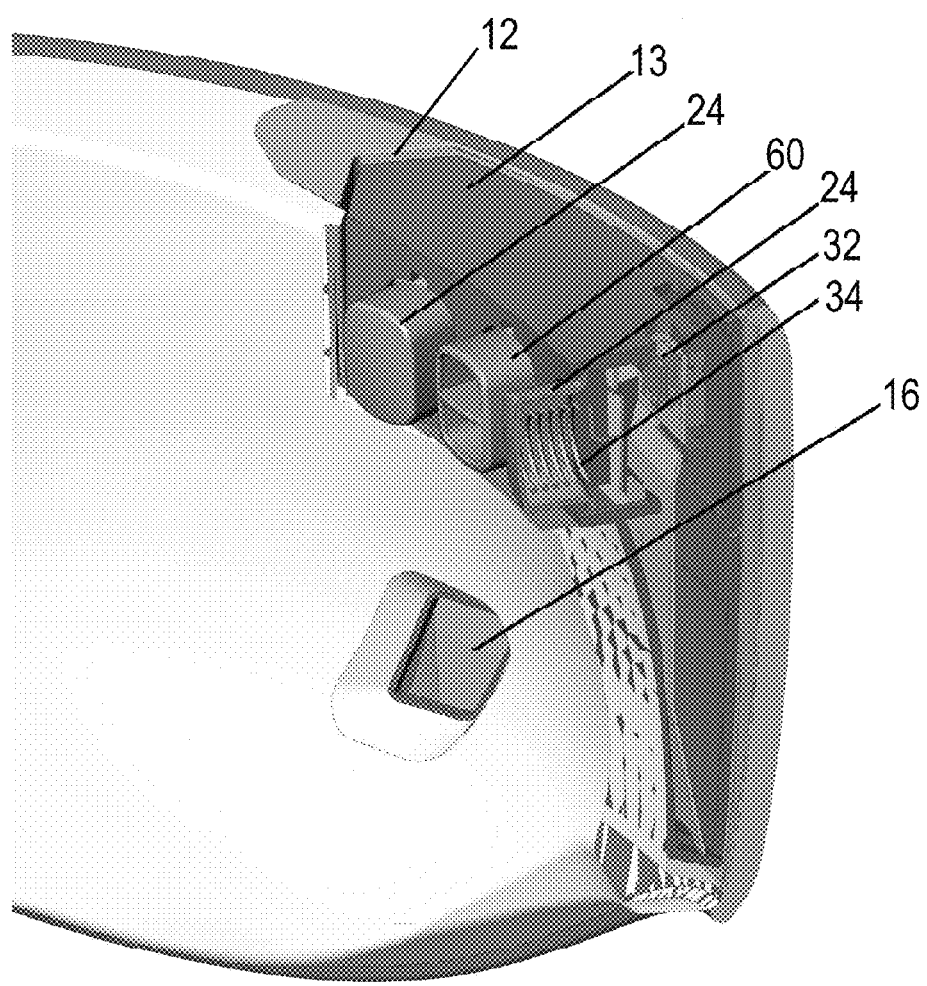
FIG. 2C illustrates a cross sectional view of the mask, according to an embodiment of the present invention.

FIG. 2C illustrates a cross sectional view of the mask where the one or more electrodes 24, pulse oximeter 60, and thermometer 29 are each housed in a tab, according to an embodiment of the present invention. Residing in each of the tabs is one or more springs 34. The one or more springs 34 are configured so that the tabs will move toward the interior of the case 13 if pressure is applied, for example pressure from a user's forehead, and resume a resting position when pressure is released. One or more sensor connectors 32 connect the one or more sensors to the mask 10. In one or more embodiments, the tabs are made of plastic.

Figure 4:
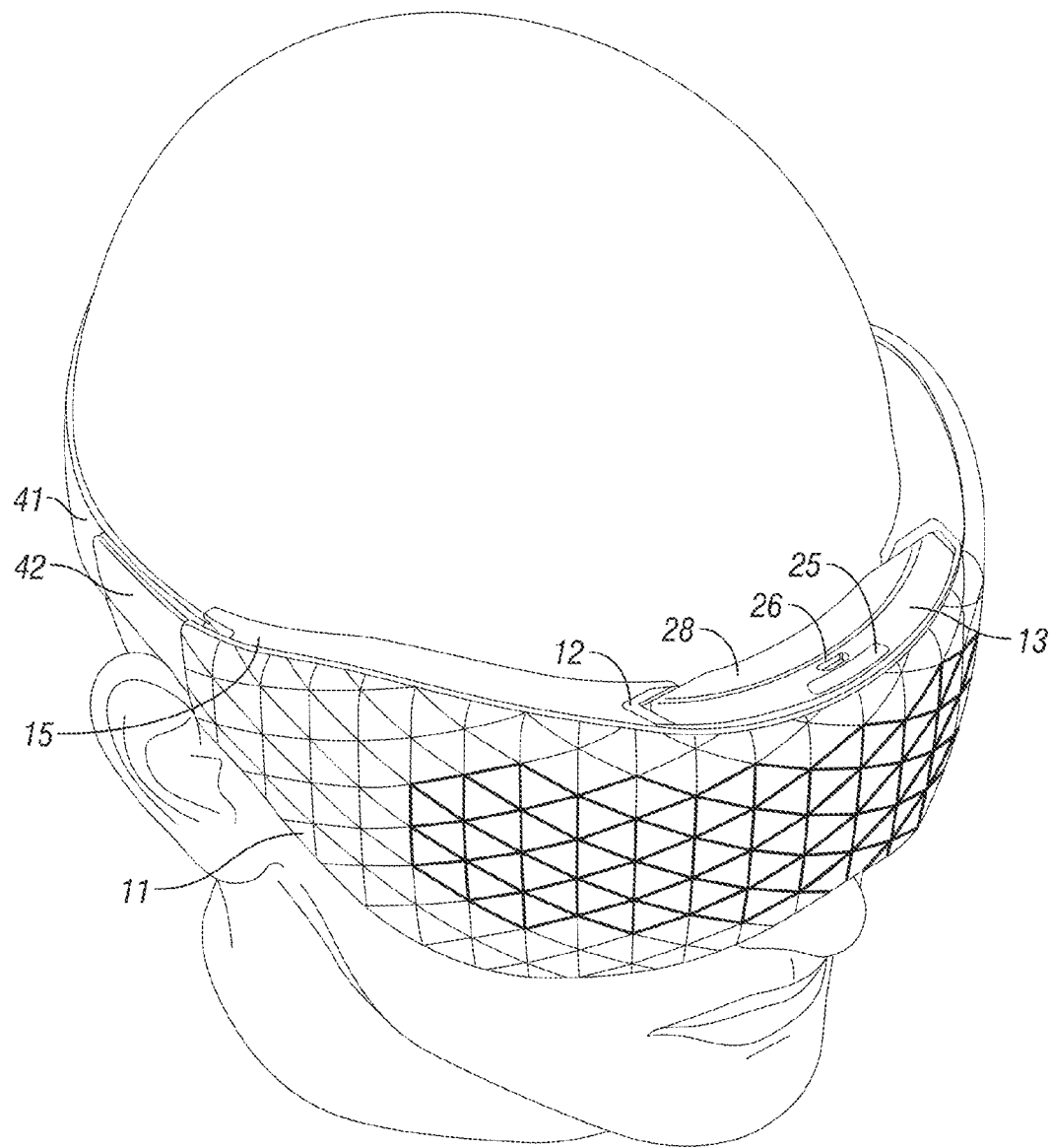
FIG. 4 illustrates a perspective view of the mask worn around a user's head, according to an embodiment of the present invention.

FIG. 4 illustrates a perspective view of the mask worn around a user's head, according to an embodiment of the present invention. The sensor strap 28 is at the top of the concave side of the case 13, such that the sensor strap 28 is positioned on the user's forehead when the mask is worn by the user. The front body side 11, the back body side 15, the cavity 12 and the mask strap 41 are shaped to maintain contact between the sensor strap 28 and the user's forehead. In one or more embodiments, the mask strap 41 is permanently attached to the case 13. The mask strap 41 length may be shortened or lengthened by adjusting Velcro 42 on the mask strap 41. In one or more embodiments, the mask strap 41 is made of fabric or rubber.

According to one or more embodiments, the two eye apertures 16 on the back body side 15 are positioned substantially opposite the user's eyes when the mask is worn by the user and are substantially aligned with the plurality of light apertures 21 on the concave side of the case 13, such that light from the printed circuit board 14 passes through the plurality of light apertures 21, through the two eye apertures 16, and reaches the user's eyes.

Figure 5:
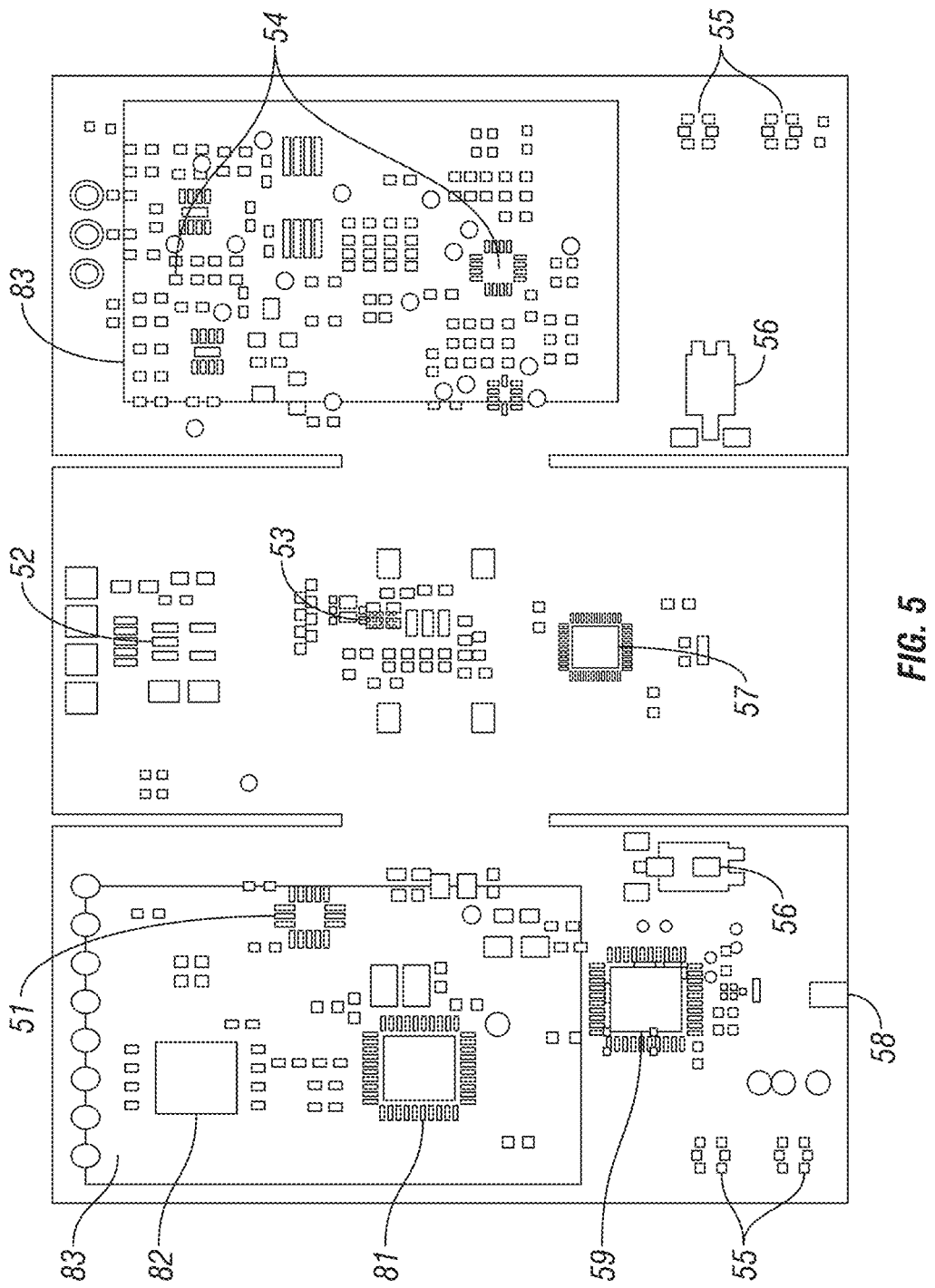
FIG. 5 is a schematic diagram showing the printed circuit board, according to an embodiment of the present invention.

FIG. 5 is a schematic diagram showing the printed circuit board 14, according to an embodiment of the present invention. The printed circuit board 14 includes an accelerometer 51, charging circuitry 52 coupled to the power input port 26 and the power button 25, battery protection and battery management circuitry 53 coupled to one or more batteries 83, biological amplifier circuitry 54 coupled to the one or more electrodes 24, one or more therapy lights 55, one or more light-emitting diode (LED) drivers 57, one or more wireless communication means 58, for sending data from the printed circuit board 14 to the device (not shown), a system on chip (SoC) microcontroller 59, a pulse oximeter driver 81, and one or more memory means 82. In the preferred embodiment, the one or more therapy lights 55 are LEDs coupled to the one or more LED drivers 57, the one or more memory means 82 include flash memory, and the one or more batteries 83 are lithium-ion batteries. The LEDs emit light in different hues. In a further embodiment, the one or more therapy lights 55 may achieve an illuminance of 7000 to 12000 lux. In one or more embodiments, the one or more therapy lights illuminate in a pulsating manner. In a further embodiment, the one or more therapy lights are configured to produce 0.2 millisecond pulses to last continuously for 30 seconds. In the preferred embodiment, the one or more wireless communication means 58 is a Bluetooth microwave antenna and the system on chip (SoC) microcontroller 59 is a Bluetooth microcontroller. In one or more embodiments, the printed circuit board 14 includes vibrator motors 56, where the vibrator motors are configured to vibrate to wake up the user.

According to one or more embodiments, the one or more electrodes 24 collect electroencephalography (EEG), electromyography (EMG), and electrooculography (EOG) data/signals from the user when the mask is worn around the user's head. The data from the one or more electrodes 24 is preamplified and filtered by the biological amplifier circuitry 54, terminally amplified and digitized by the analog-to-digital converter within the biological amplifier circuitry 54, transmitted via the bus to the processor within the SoC microcontroller 59, where digital signal processing (DSP) is performed, and saved in the internal memory of the SoC microcontroller 59 and the one or more memory means 82. In one or more embodiments, the raw data from the one or more electrodes 24 may be saved in the one or more memory means 82. On the basis of the data from these electrodes, the processor classifies the state of sleep in which the user is currently in: awake, NREM1 sleep, NREM2 sleep, NREM 3 sleep, or REM sleep.

Data from the accelerometer 51 is saved in the internal memory of the SoC microcontroller 59 and the one or more memory means 82.

According to one or more embodiments, the thermometer 29 (not shown) is a radiation thermometer. The thermometer collects thermal energy data from the user when the mask is worn around the user's head and determines the user's body temperature. The thermometer is connected to the processor via the bus such that digitized data is transmitted directly to the processor within the SoC microcontroller 59, and saved in the internal memory of the SoC microcontroller 59 and the one or more memory means 82.

In one or more embodiments, the processor in the SoC microcontroller 59 filters the digitized EEG data as follows: delta band (0.1-4.0 hertz), theta band (4.0-7.0 hertz), alpha band (8.0-16.0 hertz), beta band (16.0-31.0 hertz), and sleep spindles (12.0-14.0 hertz). The processor in the SoC microcontroller 59 calculates band power percentages based on all filtered EEG data and the band power percentages are saved in the one or more memory means 82.

In one or more embodiments, the processor within the SoC microcontroller 59 filters data from the thermometer to remove noise caused by changes in the distance between the user's head and the thermometer 29, for example noise caused by movement during sleep. The processor is configured to separate data from the thermometer into fragments, where the fragments are determined by data from the accelerometer 51. The DC signal component is filtered for each passage. This method of using the accelerometer and thermometer, makes it possible to eliminate the impact of noise on the relative temperature change readings.

Figure 6:
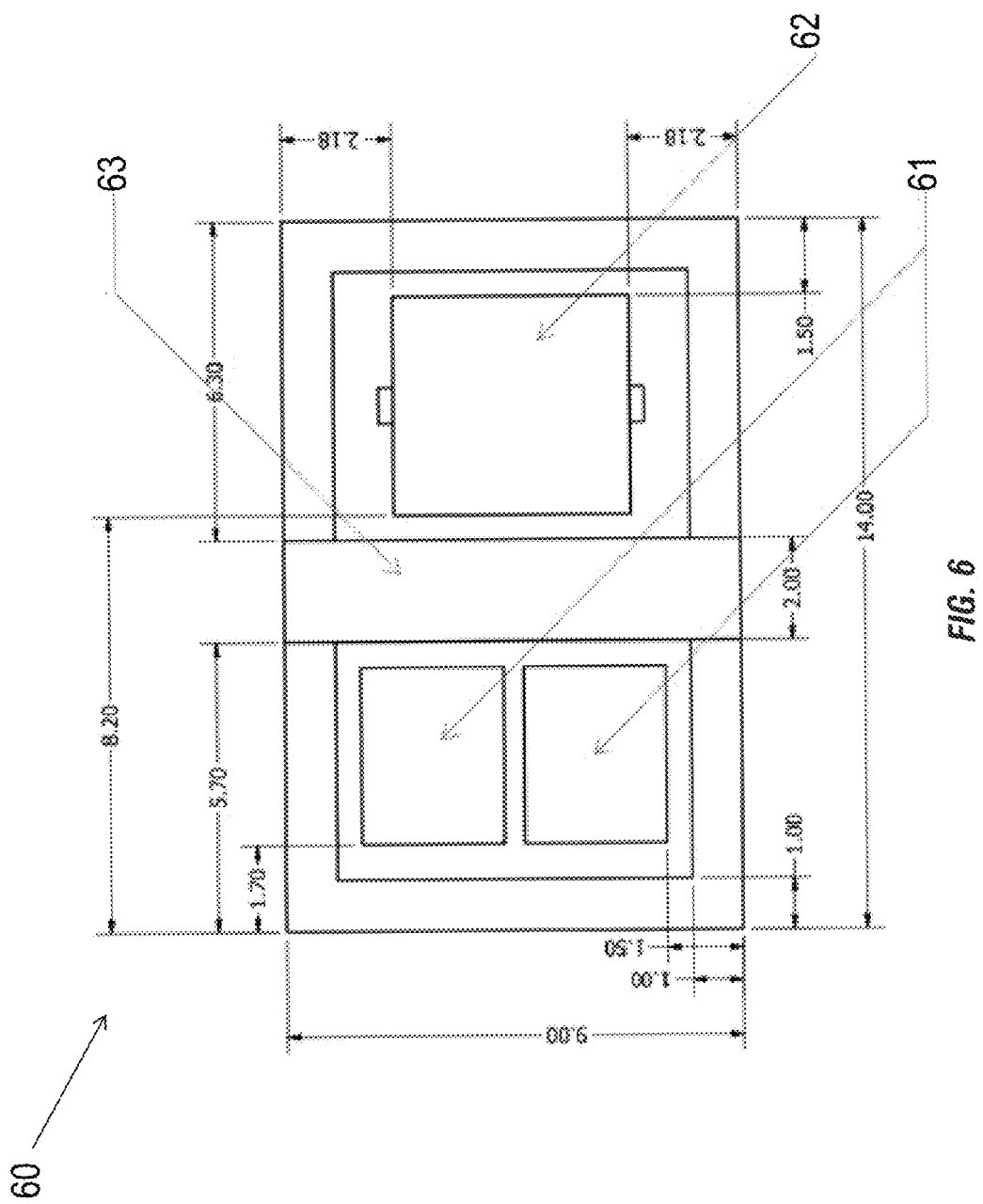
FIG. 6 is a schematic diagram showing the pulse oximeter, according to an embodiment of the present invention.

FIG. 6 is a schematic diagram showing the pulse oximeter 60, according to an embodiment of the present invention. The pulse oximeter 60 includes two or more photoemitters 61, a photodetector 62, and a partition 63. The two or more photoemitters 61 and the photodetector 62 are controlled by the pulse oximeter driver 81 in the printed circuit board 14. The two or more photoemitters 61 are coupled to one or more pulse oximeter LED drivers (not shown). The two or more photoemitters 61 emit red and infrared light. Data collected by the photodetector 62 and transmitted via the bus to the processor within the SoC microcontroller 59, where the data is processed, and saved in the internal memory of the SoC microcontroller 59 and the one or more memory means 82. In the preferred embodiment, the one or more photoemitters 61 are LEDs.

The processor within the SoC microcontroller 59 calculates the pulse and oxygen saturation in the blood using data from the photodetector 62. The processor calculates pulse by filtering the data of one of the two or more photoemitters 61 with a 1 Hz low pass filter and digitizing the data. The processor calculates a derivative from the filtered data and determines the time distance between the derivative's change from negative to positive. In the preferred embodiment, the processor calculates oxygen saturation in the blood with raw data from the photodetector 62 using the equations: "saturation of peripheral oxygen" (SpO$_2$)= 10.0002*R 3−52.887*R 2+26.871*R+98.283 and $$R = \frac{\log_{10}\left(\frac{R_{rms}*N}{R_{dc}^2}\right)}{\log_{10}\left(\frac{IR_{rms}*N}{IR_{dc}^2}\right)}$$

where $R_{rms}$ is the root mean square value of the red LED signal, $IR_{rms}$ is the root mean square value of the infrared LED signal, $R_{dc}$ is the constant red LED signal, $IR_{dc}$ is the DC signal component of infrared LEDs, and N is the number of samples.

According to one or more embodiments, the printed circuit board 14 sends data from the internal memory of the SoC microcontroller 59 and the one or more memory means 82 to the device (not shown) through the one or more wireless communication means 58. Data the internal memory of the SoC microcontroller 59 and the one or more memory means 82 include data from the pulse oximeter 60, the accelerometer 51, the one or more electrodes 24, and the thermometer. In one or more embodiments, the one or more electrodes 24 collect galvanic skin response data/signals from the user, which is used to determine when the mask is worn around the user's head. The printed circuit board 14 does not send data from the internal memory of the SoC microcontroller 59 and the one or more memory means 82 to the device (not shown) until contact is lost between the one or more electrodes 24 and the user's head, indicating removal of the mask 10 from the user's head. The printed circuit board 14 stops sending data from the internal memory of the SoC microcontroller 59 and the one or more memory means 82 if there is contact between the one or more electrodes 24 and the user's head and does not resume sending data until contact is again lost between the one or more electrodes 24 and the user's head. Sleep scoring is performed by the data management system using an artificial neural network trained using data from clinical trials, where the data management system scores sleep stages that include REM, NREM1, NREM2, and NREM3.

Figure 7:
FIG. 7 illustrates the correlation between body temperature and secretion of melatonin.

FIG. 7 illustrates the correlation between body temperature and secretion of melatonin. A body temperature curve 71 and a curve of melatonin secretion by the pineal gland 72 are illustrated, with the lowest body temperature (nadir) 73 marked on the body temperature curve 71. The secretion of melatonin is inversely proportional to body temperature, such that when a user reaches the lowest body temperature 73, there is a maximum amount of melatonin secretion. The user reaches the lowest body temperature at a later time when light exposure occurs before the lowest body temperature. In contrast, the user reaches the lowest body temperature at an earlier time when light exposure occurs after the lowest body temperature. According to one or more embodiments, the data management system uses the user's body temperature to indirectly determine the user's levels of melatonin secretion during sleep. The data management system then uses the user's levels of melatonin secretion to determine the user's circadian rhythm and light phase response curve (PRC).

According to one or more embodiments, the data management system receives data from the user through the data management system user interface, receives data from the mask, and generates a light therapy schedule. The light therapy schedule controls the operation and light intensity of the one or more therapy lights 55. In the preferred embodiment, the device is a mobile phone and the data management system is a mobile application. The user inputs a flight destination into the mobile application, the mobile application detects a current user geographical location by receiving and using Global Positioning System signals, and the mobile application presents a list of possible commercial flights between the flight destination and the current user geographical location for selection by the user. In a further embodiment, the user also provides the time the user currently wakes up.

The data management system calculates the time zone difference between the current user geographical location and the flight destination. Using a sleep algorithm based on the time zone difference, an estimate of the time when the user will currently wake up, and the length of the flight, the data management system generates a light therapy schedule. In one or more embodiments, the data management system also uses body temperature data from passengers on the same flight as the user to generate the light therapy schedule based on factors such as age and sex. In one or more embodiments, the data management system user interface presents the user with recommendations for adjusting the brightness of entertainment screens, where brightness may vary from the maximum brightness to turning off the entertainment screen. In a further embodiment, the data management system user interface presents the user with recommendations for melatonin supplement consumption. The data management system identifies the optimal time to consume melatonin supplements by processing body temperature data for several consecutive days and calculating the mean time when the user reaches the lowest body temperature. In a further embodiment, the data management system recommends via user interface when the user should avoid light and when the user should be exposed to light. The data management system makes the recommendations by processing body temperature data and calculating an average time when the user reaches the lowest body temperature.

To adjust the user's biological clock when the user travels west, the light therapy schedule will require light exposure during a period of six hours, where the six hours begins six hours before the user reaches the lowest body temperature, and require that the user avoid light after the period of six hours. Light includes sunlight and artificial light. In contrast, to adjust the user's biological clock when the user travels east, the light therapy schedule will require light exposure during a period of six hours, where the six hours begins immediately after the user reaches the lowest body temperature, and require that the user avoid light before the period of six hours. Light exposure for a full six hours during the period of six hours is optimal, but is not required to adjust the user's biological clock. As the data management system receives data from the thermometer, the data management system will adjust the light therapy schedule so that the light exposure occurs at an effective time relative to the user's lowest body temperature. In a further embodiment, the data management system adjusts the light intensity of the one or more therapy lights 55 based on the user's sleep stage. The data management system will reduce the intensity of the one or more therapy lights 55 if the user rapidly changes to a more shallow sleep stage. The light therapy schedule may require light exposure for subsequent days for users who travel a long distance.

In one or more embodiments, the data management system adjusts the light therapy schedule based on data indicating a delayed sleep onset, where the delayed sleep onset is identified by comparing the user's sleep onset with a physiological standard for sleep onset, or where the delayed sleep onset is identified by comparing the user's sleep onset with the sleep onset of the general population. The data management system also adjusts the light therapy schedule based on data indicating a delayed decrease in body temperature, where the delayed decrease in body temperature is identified by comparing the user's current body temperature pattern with the user's body temperature pattern from one or more previous days. To advance the user's circadian rhythm, the adjusted light therapy schedule will require light exposure during a period of six hours, where the six hours begins immediately after the user reaches the lowest body temperature. The schedule spans a period of at least one week, where the schedule will require light exposure during a period of six hours on each day, where the six hours begin immediately after the user reaches the lowest body temperature.

In one or more embodiments, the user may turn on a delay function in the data management system. During a light therapy schedule with the delay function turned on, the data management system in one or more embodiments will not begin light exposure if the user's sleep stage is NREM1 or if the user is about to wake up. Instead, the data management system will delay light exposure until the user's sleep stage is NREM2, NREM3, or REM. In a further embodiment, the user may turn on a wake-up function, where the data management system is configured to wake up the user when the user's sleep stage is NREM1 or NREM2, using light from the one or more therapy lights 55. In a further embodiment, the data management system is configured to wake up the user using both the one or more therapy lights 55 and the vibrator motors 56 if the user continues to sleep after the system attempts to wake up the user using just the one or more therapy lights 55.

In one or more embodiments, the data management system alerts the user through the user interface when the data management system detects a sleep disorder such as sleep apnea. During a light therapy schedule, the data management system will monitor the user's pulse and oxygen saturation in the blood. Based on such data obtained by the pulse oximeter in combination with the sleep stage data, an accurate determination of sleep apnea will be determined, i.e. breathing has stopped during sleep and not while the user was awake. A decrease in oxygen saturation and bradycardia followed by tachycardia will suggest that the user has a sleep disorder.

According to embodiments of the present invention, there is a sleep mask apparatus for use in a system for treating sleep disorder symptoms. The sleep mask apparatus comprises: a body including a front body side, a back body side, a cavity at the center of the body, a mask strap, a case for housing a printed circuit board, and a power input port operatively connected to the printed circuit board and configured to supply power to the printed circuit board from an external power source. The printed circuit board includes an accelerometer and one or more lights. The case is removably inserted into the cavity, the cavity includes one or more cavity magnets attached to an inside surface of the cavity.

The case further comprises a sensor strap wherein one or more dry electrodes, a pulse oximeter and a thermometer are located on the sensor strap. The dry electrodes, pulse oximeter and thermometer sit on movable tabs by way of a spring inside each tab, adjusting for the pressure of the mask against the user's forehead. The pulse oximeter, the thermometer, and the one or more dry electrodes are connected to the printed circuit board and configured to transmit collected data to the printed circuit board. The case further comprising a plurality of light apertures on the case. Two eye apertures are on the back body side, positioned substantially opposite the user's eyes and are substantially aligned with the plurality of light apertures when the mask is worn. The mask is configured to communicate with an external computing device having a data management system (software application).

According to one or more embodiments of the present invention, there is a method for treating sleep disorder systems using a sleep mask on a user. In one embodiment, the method comprises: receiving data from an accelerometer on the sleep mask, receiving data from a thermometer on the sleep mask and, receiving signals from one or more electrodes on the sleep mask; calculating an average time when the user reaches a lowest body temperature; generating a light therapy schedule and adjusting the schedule based on periodically received data including temperature data of the user; controlling and operating a light intensity of one or more lights on the sleep mask. The method further comprises adjusting the schedule by the periodically received data which further includes current sleep stage data as receiving through the signals of the electrodes on the sleep mask. The method further comprises: receiving through a pulse oximeter on the sleep mask, data on pulse and oxygen saturation in the blood; filtering the data and calculating pulse; and calculating oxygen saturation in the blood. Calculations are determined via the processor in the sleep mask and may include data transmitted from an external data management system (software of an external computing device in communication with the sleep mask). Generating the light therapy schedules and the steps of controlling, operating and adjusting may further be conducted with the communication between the external device with data management system.

Throughout the description and drawings, example embodiments are given with reference to specific configurations. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments of the foregoing description.

What is claimed is:

1. A system for treating sleep disorder symptoms, the system comprising:
   a mask configured to establish a snug fit against a user's eyes, the mask including
      a printed circuit board, the printed circuit board including an accelerometer and one or more therapy lights,
      a case configured to house the printed circuit board, the case including
         a power button and
         a power input port, wherein the power input port is configured to supply power to the printed circuit board from an external power source,
         one or more electrodes, a pulse oximeter, a thermometer, and
         a plurality of light apertures, wherein the plurality of light apertures are positioned substantially opposite the user's eyes, such that when the mask is worn, light from the one or more therapy lights passes through the plurality of light apertures to reach the user's eyes,
      wherein the one or more electrodes, the pulse oximeter, and the thermometer are configured to be positioned on the user's forehead when the mask is worn,
      wherein the pulse oximeter, the thermometer, and the one or more electrodes are connected to the printed circuit board, configured to measure data including a body temperature of a user, and transmit data to the printed circuit board, and
      wherein the mask is made of an opaque light-blocking material, and
   a device coupled to the mask, the device including a user interface and a data management system that is configured to
      generate a schedule based on a current user sleep schedule and a target user sleep schedule, and
      adjust the schedule based on data received from the mask,
      wherein the schedule controls operation and light intensity of the one or more therapy lights.

2. The system according to claim 1, the printed circuit board further comprising one or more wireless communication means for sending data from the printed circuit board to a device, wherein the device includes the data management system.

3. The system according to claim 2, the printed circuit board further comprising one or more memory means, wherein the printed circuit board is configured to send data to the device after the user removes the mask from the user's head, and wherein the device includes the data management system.

4. The system according to claim 1, wherein the data management system is configured to adjust the schedule based on data indicating a delayed sleep onset or a delayed decrease in body temperature, wherein said data includes body temperature of the user as measured by the thermometer on the mask.

5. The system according to claim 1, wherein the data management system is configured to adjust the schedule based on data received from the mask indicating a current sleep stage that is shallow or a rapid change to a more shallow sleep stage.

6. The system according to claim 1, wherein the data management system is configured to provide brightness recommendations for entertainment screens to the user, and wherein brightness recommendations for entertainment screens are presented to the user through the user interface.

7. The system according to claim 1, wherein the data management system is configured to provide melatonin intake recommendations to the user, and wherein melatonin intake recommendations are presented through the user interface.

8. The system according to claim 1, wherein the current user sleep schedule is based on a current user geographical location, the target user sleep schedule is based on a target geographical location, and the user provides the target geographical location through the user interface.

9. The system according to claim 1, wherein the case further comprises one or more case magnets attached on an outer surface of the case, and wherein the mask further comprises a cavity at a center of the mask, the cavity configured for removably receiving the case therein, the cavity including one or more cavity magnets attached at an inside surface of the cavity, the one or more cavity magnets aligned with and attracted to one or more case magnets, thereby releasably securing the case inside the cavity.

10. A system for treating sleep disorder symptoms, the system comprising:
  a mask configured to establish a snug fit against a user's eyes, the mask including
    a printed circuit board, the printed circuit board including an accelerometer and one or more therapy lights,
    a case configured to house the printed circuit board,
    one or more electrodes, a pulse oximeter, a thermometer, and a plurality of light apertures,
    wherein the one or more electrodes, the pulse oximeter, and the thermometer are configured to be positioned on the user's forehead when the mask is worn,
    wherein the pulse oximeter, the thermometer, and the one or more electrodes are connected to the printed circuit board, configured to measure data including a body temperature of a user, and transmit data to the printed circuit board, and
    wherein the mask is made of an opaque light-blocking material, and
  a data management system that is configured to
    generate a schedule based on a current user sleep schedule and a target user sleep schedule, and
    adjust the schedule based on data received from the mask,
    wherein the schedule controls operation and light intensity of the one or more therapy lights.

11. The system according to claim 10, the printed circuit board further comprising one or more wireless communication means for sending data from the printed circuit board to a device, wherein the device includes the data management system, and wherein the device is coupled to the mask.

12. The system according to claim 11, the printed circuit board further comprising one or more memory means, wherein the printed circuit board is configured to send data to the device after the user removes the mask from the user's head, wherein the device includes the data management system, and wherein the device is coupled to the mask.

13. The system according to claim 10, wherein the data management system is configured to adjust the schedule based on data indicating a delayed sleep onset or a delayed decrease in body temperature, wherein said data includes the body temperature of the user as measured by the thermometer on the mask.

14. The system according to claim 10, wherein the data management system is configured to adjust the schedule based on data received from the mask indicating a current sleep stage that is shallow or a rapid change to a more shallow sleep stage.

15. The system according to claim 10, wherein the data management system is configured to provide brightness recommendations for entertainment screens to the user, and wherein brightness recommendations for entertainment screens are presented to the user through a user interface.

16. The system according to claim 10, wherein the data management system is configured to provide melatonin intake recommendations to the user, and wherein melatonin intake recommendations are presented through the user interface.

17. The system according to claim 10, wherein the current user sleep schedule is based on a current user geographical location, the target user sleep schedule is based on a target geographical location, and the user provides the target geographical location through the user interface.

18. The system according to claim 10, wherein the case further comprises one or more case magnets attached on an outer surface of the case, and wherein the mask further comprises a cavity at a center of the mask, the cavity configured for removably receiving the case therein, the cavity including one or more cavity magnets attached at an inside surface of the cavity, the one or more cavity magnets aligned with and attracted to one or more case magnets, thereby releasably securing the case inside the cavity.

* * * * *